(12) United States Patent
Hu et al.

(10) Patent No.: US 11,879,139 B1
(45) Date of Patent: Jan. 23, 2024

(54) SCALABLE METHODS FOR PURIFICATION OF RECOMBINANT VIRUSES

(71) Applicant: PORTON ADVANCED SOLUTIONS LTD., Suzhou (CN)

(72) Inventors: Dichao Hu, Jiangsu (CN); Chuanzhen Pi, Jiangsu (CN); Kai Weng, Jiangsu (CN); Jinbo Guo, Jiangsu (CN); Hailong Liu, Jiangsu (CN); Yangzhou Wang, Jiangsu (CN); Weimeng Zhang, Jiangsu (CN); Jun Hua, Jiangsu (CN)

(73) Assignee: PORTON ADVANCED SOLUTIONS LTD., Suzhou (CN)

( * ) Notice: Subject to any disclaimer, the term of this patent is extended or adjusted under 35 U.S.C. 154(b) by 0 days.

(21) Appl. No.: 18/049,627

(22) Filed: Oct. 25, 2022

(30) Foreign Application Priority Data

Sep. 20, 2022 (WO) ................ PCT/CN2022/119927

(51) Int. Cl.
*C12N 7/02* (2006.01)
*C07K 1/36* (2006.01)

(52) U.S. Cl.
CPC . *C12N 7/02* (2013.01); *C07K 1/36* (2013.01)

(58) Field of Classification Search
None
See application file for complete search history.

(56) References Cited

U.S. PATENT DOCUMENTS

| | | | | |
|---|---|---|---|---|
| 2014/0227766 A1* | 8/2014 | Gagnon | ............... | B01D 15/363 252/189 |
| 2016/0058857 A1* | 3/2016 | Spencer | ......... | A61K 39/001171 435/325 |
| 2018/0163182 A1* | 6/2018 | Broadt | ................ | B01D 15/363 |
| 2022/0033849 A1* | 2/2022 | Mayani | ............. | B01D 15/1864 |

OTHER PUBLICATIONS

Hao Li et al., "A hydrophobic interaction chromatography strategy for purification of inactivated foot-and-mouth disease virus", Protein Expression and Purification 113 (2015) 23-29.
Jeremy Lee et al., "Principles and applications of steric exclusion chromatography", Journal of Chromatography A, 1270 (2012) 162-170.
First Office Action of the counterpart Chinese application 202211253358.6, dated Sep. 12, 2023.

* cited by examiner

*Primary Examiner* — Benjamin P Blumel
(74) *Attorney, Agent, or Firm* — Jun He Law Offices P.C.; Yi Zhang

(57) ABSTRACT

The present disclosure provides a scalable and cost-effective method of purifying recombinant viruses, such as recombinant lentiviruses. Also provided herein are recombinant viruses (e.g., lentiviruses) purified using the methods provided herein, which have a low level of impurities and high activity retention.

25 Claims, 4 Drawing Sheets

US 11,879,139 B1

SCALABLE METHODS FOR PURIFICATION OF RECOMBINANT VIRUSES

CROSS-REFERENCE TO RELATED APPLICATIONS

This application claims priority to a PCT International Patent Application no. PCT/CN2022/119927, filed Sep. 20, 2022, the disclosure of which is incorporated herein by reference in their entirety.

FIELD OF THE INVENTION

The present invention generally relates to a method for purifying recombinant viruses. In particular, the method of the invention relates to large scale recovery of fragile viruses, such as lentiviral vectors, under conditions complying with regulatory requirements.

BACKGROUND OF THE INVENTION

Several viruses have been engineered as vectors for gene therapy, such as retroviruses (e.g., lentivirus), adenoviruses, adeno-associated viruses (AAV), herpes simplex viruses (HSV) and vaccinia viruses. To obtain recombinant viruses that meet the requirements of drug application, purification is required to remove impurities and maximally retain the activity of the viruses during the purification.

Existing purification process generally involves steps such as cell culture harvest, clarification, ultrafiltration concentration, nuclease digestion, column chromatography, concentration and diafiltration (FIG. 1, left panel). Among these steps, column chromatography is a key step to remove impurities. Conventional column chromatography used for purification of recombinant viruses (e.g., lentiviruses) includes molecular sieve chromatography (also named size exclusion chromatography) (e.g., 4FF and 6FF), anion exchange chromatography (e.g., Fractogel® EMD DEAE and Capto Q), affinity chromatography (e.g., Heparin), anion exchange membrane chromatography (e.g., Mustang Q, Sarotbind Q and CIM DEAE) and multimodal chromatography (e.g., Capto Core 700, which can also be considered as a size exclusion chromatography).

The purification principle of ion exchange chromatography and affinity chromatography is based on a bind-elute mode. After viral vectors are bound to chromatographic medium, impurities are removed by washing, and the viral vectors bound to the medium can be eluted off the medium by an elution buffer having a NaCl solution of high concentration (such as 0.6~1.0 mol/L). However, high salt concentration during elution often deactivates viral vectors or recombinant viruses, thereby leading to a decrease in the transduction/transfection efficiency of the viral vectors and further affects the efficacy of the therapeutics encoded by the polynucleotides carried by the viral vectors.

The purification principle of molecular sieve chromatography is based on a flow-through mode, where the target species (e.g., recombinant virus particles) and impurities are separated according to the molecular size. Molecular sieve chromatography-based purification usually has a dilution effect on the target sample, which makes it difficult to scale up due to its own load limitation.

The principle of multimodal chromatography is a combination of the principle of molecular sieve chromatography with the principle of ion exchange, that is, the target species (e.g., recombinant virus particles) are harvested based on the flow-through mode, while process-related small molecular impurities (such as proteins derived from packaging cells (i.e., host cell proteins (HCPs)) and/or DNAs derived from packaging cells (i.e., host cell DNAs (HCDs))) enter the medium pores and are absorbed in an ion-exchange mode to achieve effective separation. Accordingly, the multimodal chromatography also has the disadvantages of molecular sieve chromatography, for example, a dilution effect on the sample.

In addition, the one-step chromatography used in the conventional method is difficult to control process-related impurities (especially HCP and HCD) at a relatively low level and cannot meet relevant regulatory requirements and quality standards for cell and gene therapy (CGT) drugs.

It would be even more challenging for viruses (e.g., lentiviruses) produced in suspension cells, because it usually requires high cell densities (such as 3~4×10$^6$ cells/mL, even some cases more than 10×10$^6$ cells/mL) for virus packaging to obtain high titers of viruses (e.g., lentivirus), which results in HCPs and HCDs of more than 10 times higher than that of adherent cells. For example, in the lentiviral harvest supernatant packaged by suspension cells, the HCP content is usually about 40-200 µg/mL, and the HCD content is usually 10-30 µg/mL. After purification using the conventional method illustrated in FIG. 1, the purified viral preparation usually (e.g., lentiviral preparation) has an HCP content of 1-10 µg/mL and a HCD content of 1-3 µg/mL. As a key material used in CAR-T production, lentiviral preparation with the above-mentioned levels of impurities will greatly compromise the quality of the cell therapy product.

Therefore, need exists for scalable and cost-effective methods of purifying recombinant viruses (especially extremely fragile viral vectors, such as lentiviral vectors) to obtain purified recombinant viruses with low impurity and high activity for clinical uses.

BRIEF SUMMARY OF THE INVENTION

In one aspect, the present disclosure provides a method of purifying a population of recombinant virus particles, said method comprising:
- obtaining a sample comprising the recombinant virus particles;
- subjecting the sample to a steric exclusion chromatography (SXC) column comprising a SXC medium in the presence of a nonionic organic polymer rendering the recombinant virus particles bound to the SXC medium, wherein the nonionic organic polymer is chemically inert to both the SXC medium and the recombinant virus particles;
- eluting the SXC column with an elution buffer to obtain a preparation of the recombinant virus particles; and
- subjecting the preparation of the recombinant virus particles to a size exclusion chromatography (SEC) column to obtain a flow-through liquid comprising the recombinant virus particles.

In certain embodiments, the SEC medium is a multimodal chromatographic medium, such as Capto Core700, Lyer700, Capto Core400, Mix Q-90, Seplife Suncore 700, Monomix 500, or Monomix 1000

In certain embodiments, the SEC column has a bed height of about 5-10 cm.

In certain embodiments, the SXC medium is selected from the group consisting of: 4FF (e.g., Sepharose 4FF, Bestarose 4FF, NW Rose 4FF, Seplife 4FF), 6FF (e.g., Sepharose 6FF, Bestarose 6FF, NW Rose 6FF, Seplife 6FF), NW Dex G-25, NW Super 75, NW Super 100, NW Super 150, NW Super 200, Seplife 6B, Seplife G25, Seplife G75 and Seplife G100. In certain embodiments, the SXC medium is Sepharose 4FF.

In certain embodiments, the SXC column has a bed height of about 5-10 cm.

In certain embodiments, the elution buffer comprises a NaCl of 0.3-0.5 mol/l (e.g., 0.4 mol/l). In certain embodiments, the elution buffer does not contain the nonionic organic polymer.

In certain embodiments, the nonionic organic polymer is polyethylene glycol (PEG).

In certain embodiments, the PEG has an average molecular weight between about 4,000 (PEG4000) grams per mole and about 15,000 (PEG15000), preferably between about 4,000 (PEG4000) grams per mole and about 8,000 (PEG8000).

In certain embodiments, the PEG has an average molecular weight of about 6,000 (PEG6000) grams per mole.

In certain embodiments, the PEG has a concentration of about 10-15% (w/v).

In certain embodiments, the recombinant virus comprises a transgene encoding a therapeutic protein or fragment thereof.

In certain embodiments, the therapeutic protein is selected from the group consisting of: chimeric antigen receptor (CAR), an enzyme, cytokine, chemokine, hormone, antibody, anti-oxidant molecule, engineered immunoglobulin-like molecule, single chain antibody, fusion protein, immune co-stimulatory molecule, immunomodulatory molecule, a transdomain negative mutant of a target protein, toxin, conditional toxin, antigen, transcription factor, structural protein, reporter protein, subcellular localization signal, tumor suppressor protein, growth factor, membrane protein, receptor, vasoactive protein or peptide, anti-viral protein or ribozyme, or a derivative thereof, or a micro-RNA.

In certain embodiments, the sample comprises at least $1 \times 10^6$ TU/ml recombinant virus particles.

In certain embodiments, the sample is prepared from a culture of suspension cells. In certain embodiments, the sample is clarified supernatants. In certain embodiments, the sample is prepared from cell culture lysate.

In certain embodiments, the suspension cells are selected from the group consisting of: HEK293 T cells or subtypes, HEK293 cells and 293 EBNA-1 cells or subtypes.

In certain embodiments, the methods provided herein further comprises adding a nuclease (e.g., Benzonase (Merk) or BenzoNuclease (Novoprotein)) or other brand GMP endonuclease to the culture before preparing the supernatant or lysate.

In certain embodiments, the population of recombinant virus particles after purification contains less than 1 ug/ml (e.g., less than 0.8 ug/ml, less than 0.6 ug/ml, less than ug/ml, less than 0.2 ug/ml, or less than 0.1 ug/ml) proteins derived from the suspension cells and/or less than 0.8 ug/ml (e.g., less than 0.6 ug/ml, less than 0.4 ug/ml, less than 0.2 ug/ml, or less than 0.1 ug/ml) DNAs derived from the suspension cells.

In certain embodiments, the population of recombinant virus particles after purification is capable of infecting a population of host cells rendering more than 70% of the host cells expressing the therapeutic protein or fragment thereof at a multiplicity of infection (MOI) of no more than 3.

In certain embodiments, the method provided herein further comprises subjecting the flow-through liquid comprising the recombinant virus particles to sterile filtration, ultrafiltration or diafiltration. In certain embodiments, the sterile filtration is performed prior to the ultrafiltration or diafiltration.

In certain embodiments, the ultrafiltration is a tangential flow filtration.

In certain embodiments, the tangential flow filtration is carried out by a hollow fiber module (e.g., hollow fiber module having a pore size of 300-750 KD).

In certain embodiments, the recombinant virus is selected from the group consisting of: retrovirus (e.g., lentivirus), adenovirus, adeno-associated virus (AAV), herpesvirus (e.g., herpes simplex virus), poxvirus, baculovirus, papillomavirus, and papovavirus (e.g., SV40), Virus-like particles (e.g. HCV, HPV) and inactivated virus vaccine (COVID 19 vaccines, Rabies vaccines).

In certain embodiments, the recombinant virus is a retrovirus (e.g., lentivirus) or an AAV.

In another aspect, the present disclosure provides a method of purifying a population of recombinant virus particles, said method comprising:

obtaining a sample comprising the recombinant virus particles;

subjecting the sample to a SEC column comprising a SEC medium to obtain a flow-through liquid comprising the recombinant virus particles;

subjecting the flow-through liquid to a SXC column comprising a SXC medium in the presence of a nonionic organic polymer rendering the recombinant virus particles bound to the SXC medium, wherein the nonionic organic polymer is chemically inert to both the SXC medium and the recombinant virus particles; and eluting the SXC column with an elution buffer to obtain a preparation of the recombinant virus particles.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION OF THE INVENTION

Figure 1:
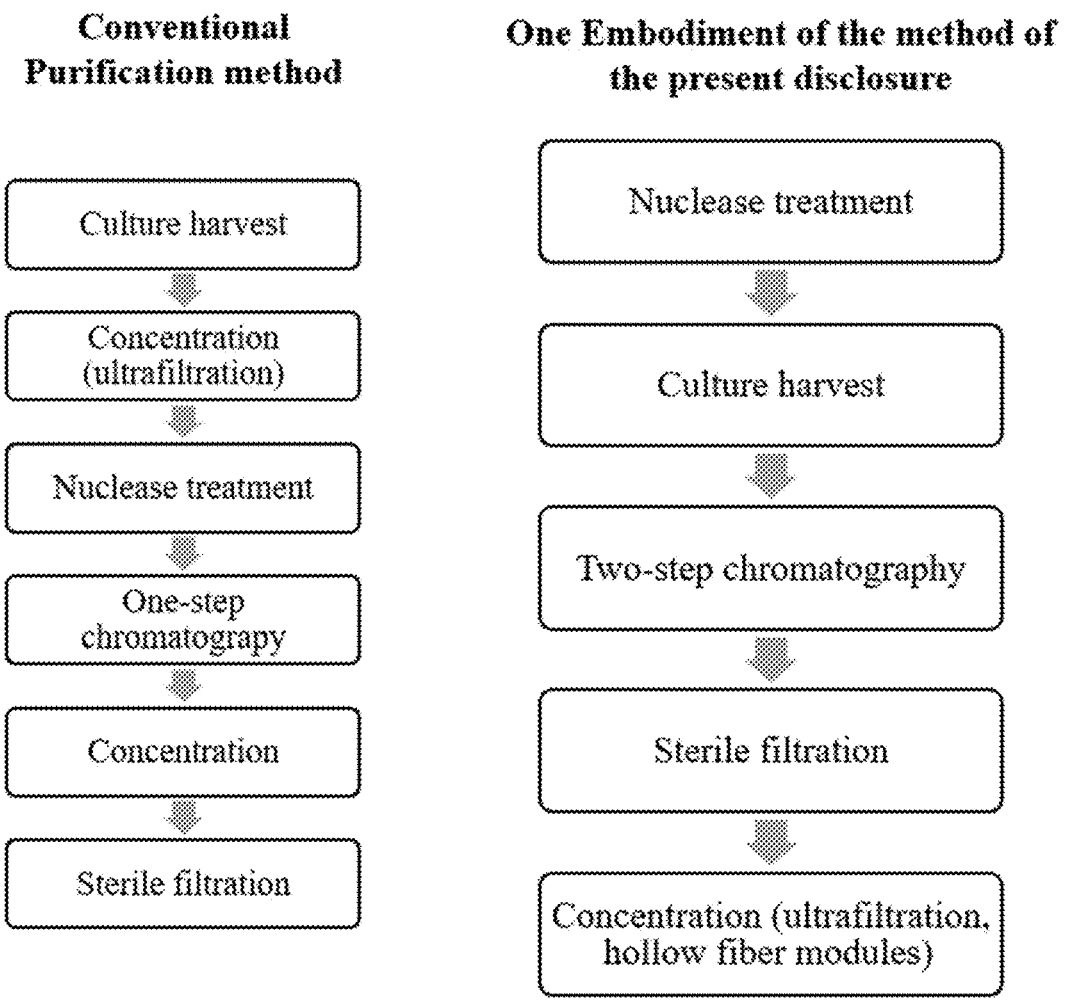
FIG. 1 shows the flowchart of the conventional purification method (left) and an exemplary method of the present disclosure (right).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Definition

It is to be understood that both the foregoing general description and the following detailed description are exemplary and explanatory only and are not restrictive of the invention as claimed. In this application, the use of the singular includes the plural unless specifically stated otherwise. In this disclosure, the term "or" is used to mean "and/or" unless explicitly indicated to refer to alternatives only or the alternatives are mutually exclusive. As used herein "another" may mean at least a second or more. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

As used herein, the singular forms "a", "an" and "the" include plural references unless the context clearly dictates otherwise.

As used herein, the term "recombinant" with respect to virus particles indicates that the virus particles have been artificially or synthetically (non-naturally) altered by human intervention. The alteration can be conducted on the virus particles within, or removed from, its natural environment or state. For example, a recombinant virus particle refers to a virus particle that comprises a recombinant polynucleotide sequence.

As used herein, the term "virus" refers to whole virus (also identified as virus particles), viral vector, virus like particles (VLPs) and viral proteins unless otherwise identified.

A "lentivirus", as used herein, refers to a viral species belonging to a class of virus named retrovirus. Lentiviruses are RNA viruses with a packaging capacity up to 8 Kb, with the ability to confer long-term transgene expression. Lentivirus has a reverse transcriptase enzyme that converts RNA into DNA, which migrates to the nucleus of a host cell and integrates into the host genome. Lentiviruses are enveloped particles that bud from the plasma membrane of the host cell.

As used herein, the term "packaging cell" refers to a cell line that produces the necessary viral proteins for encapsidation of the desired recombinant RNA. In certain embodiments, the packaging cell does not contain a packaging signal for packaging viral RNA ($\psi$ sequence), such that there is no release of wild-type helper viruses despite of the presence of, e.g., the intact gag, pol and env genes, and would only package the transfected proviral DNA vectors containing the $\psi$ sequence required for packaging. Exemplary packaging cells include, but not limited to, a human cell (e.g., HEK293, HEK293T, HEK293FT, 293 EBNA-1 cells (a HEK293 cell line stably expressing the Epstein-Barr virus nuclear antigen-1), Te671, HT1080, CEM), a muridae cell (NIH-3T3), a mustelidae cell (Mpi), and a canid cell (D17). In certain embodiments, the packaging cell is suspension HEK293T G2S. The HEK293T G2S can be produced through clone screening, suspension adaptation and lentivirus packaging optimization.

As used herein, the term "suspension cells", used interchangeable with the term "non-adherent cells", refers to cells in culture where the majority or all of the cells in culture are present in suspension, and the minority or none of the cells in the culture container (e.g., bioreactor) are attached to the container surface or to another surface within the container (e.g., bioreactor). The "suspension cells" may have more than 50%, 60%, 70%, 80%, 90% or 95% of the cells in suspension, and not attached to a surface on or in the culture container (e.g., bioreactor).

As used herein, the term "bed height" refers to the height of a bed of a chromatographic medium (e.g., a SEC medium, or a SXC medium) formed in a column.

The term "host cell" means a cell that has been transformed, or is capable of being transformed, with a nucleic acid sequence and thereby expresses a protein of interest. The term includes the progeny of the parent cell, whether or not the progeny is identical in morphology or in genetic make-up to the original parent cell, so long as the gene of interest is present. In some embodiments, the term "host cell" may also refer to a cell that is used to package recombinant virus particles, in which case, the term "host cell" is used interchangeably with the term "packaging cell".

The term "nucleic acid" or "polynucleotide" as used herein refers to deoxyribonucleic acids (DNA) or ribonucleic acids (RNA) and polymers thereof in either single- or double-stranded form. Unless otherwise indicated, a particular polynucleotide sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (see Batzer et al., *Nucleic Acid Res*. 19:5081 (1991); Ohtsuka et al., *J. Biol. Chem*. 260:2605-2608 (1985); and Rossolini et al., *Mol. Cell. Probes* 8:91-98 (1994)).

As used herein, a "vector" refers to a composition comprising a nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform, or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

As used herein, the term "large-scale" or "large scale" refers to total cell fermentation volumes of greater than about 2 liters (e.g., about 3 liters, about 4 liters, about 5 liters, about 6 liters, about 7 liters, or about 8 liters), or the number of cells harvested from a fermentation volume greater than about 2 liters (e.g., about 3 liters, about 4 liters, about 5 liters, about 6 liters, about 7 liters, or about 8 liters). The large-scale purification method of the present disclosure is applicable to clinical size lots which represent, but are not limited to, approximately 100-250 liter of fermentations.

Methods for Purifying Recombinant Viruses

Viral vectors are widely used in the field of cell and gene therapy (CGT). For example, lentiviral vectors are frequently used in CGT because of their high transduction efficiency and sustainable and stable expression of target genes after integration into the genome. However, viral vectors (e.g., retroviral vectors, in particular lentiviral vectors) are fragile and sensitive to high salt concentration and shearing forces. Lentiviral vectors can be produced in either adherent cells or suspension cells. A conventional method of purifying lentiviral vectors is illustrated in FIG. 1, which is time-consuming and results in high impurities and compromised activity of the purified recombinant virus particles.

The present disclosure provides a novel method for efficient, cost-effective, and scalable purification of recombinant virus particles, such as retroviral vectors, in particular lentiviral vectors. In one aspect, the present disclosure provides a method of purifying a population of recombinant virus particles, said method comprising: obtaining a sample (e.g., supernatant or lysate) comprising the recombinant virus particles; subjecting the sample (e.g., supernatant or lysate) to a size exclusion chromatography (SEC) column comprising a SEC medium to obtain a flow-through liquid comprising the recombinant virus particles; subjecting the flow-through liquid to a steric exclusion chromatography (SXC) column comprising a SXC medium in the presence of a nonionic organic polymer rendering the recombinant virus particles bound to the SXC medium, wherein the nonionic organic polymer is chemically inert to both the SXC medium and the recombinant virus particles; and eluting the SXC column with an elution buffer to obtain a preparation of the recombinant virus particles. The term "preparation of the recombinant virus particles", as used herein, may refer to a product obtained immediately after the SXC step in some embodiments. In other embodiments, the term "preparation of the recombinant virus particles" may refer to a product obtained after further purification steps such as sterile filtration, ultrafiltration and diafiltration. In some embodiments, the term "preparation of the recombinant virus particles" may refer to a product for clinical use.

It can be understood that in some embodiments of the method disclosed herein, the SEC step and the SXC step may be inverted. In certain embodiments, the sample (e.g., supernatant or lysate) is subjected to the SXC column first to obtain a preparation of the recombinant virus particles, which is then subjected to the SEC column to obtain a flow-through liquid comprising the recombinant virus particles. The flow-through liquid comprising the recombinant virus particles may further be subjected to sterile filtration, ultrafiltration and diafiltration before obtaining a preparation of the recombinant virus particles for clinical uses. Accordingly, the present disclosure also provides a method of purifying a population of recombinant virus particles, said method comprising: obtaining a sample (e.g., supernatant or lysate) comprising the recombinant virus particles; subjecting the sample (e.g., supernatant or lysate) to a SXC column comprising a SXC medium in the presence of a nonionic organic polymer rendering the recombinant virus particles bound to the SXC medium and eluting the SXC column with an elution buffer to obtain a preparation of the recombinant virus particles, wherein the nonionic organic polymer is chemically inert to both the SXC medium and the recombinant virus particles; subjecting the preparation of the recombinant virus particles to a SEC column to obtain a flow-through liquid comprising the recombinant virus particles. The flow-through liquid comprising the recombinant virus particles may be further subjected to sterile filtration, ultrafiltration and diafiltration.

Without wishing to be bound by any theory, it is believed that conducting the SEC step after the SXC step would help removing the nonionic organic polymer from the sample and meanwhile may compromise the recovery rate. Accordingly, if a high recovery rate is desirable, the SEC step is preferably conducted prior to the SXC step, in some embodiments. In other embodiments, if the ultimate recovery rate is acceptable, it is preferable to conduct the SEC step after the SXC step.

In certain embodiments, the recombinant virus particles comprise a transgene encoding a therapeutic protein or fragment thereof. The transgene encoding a therapeutic protein will depend on the specific use for which the recombinant virus is intended. The therapeutic protein may be a protein deficient or absent in a subject affected with a pathology, may be an antigen that induces vaccination of the recipient subject against the antigen, or may be a protein expressed on an immune cell that pulls the immune cell specifically towards to a cell to be eliminated and activates the immune cell upon binding to the cell to be eliminated. For example, the therapeutic protein may be chimeric antigen receptor (CAR), an enzyme, cytokine, chemokine, hormone, antibody, anti-oxidant molecule, engineered immunoglobulin-like molecule, single chain antibody, fusion protein, immune co-stimulatory molecule, immunomodulatory molecule, a transdomain negative mutant of a target protein, toxin, conditional toxin, antigen, transcription factor, structural protein, reporter protein, subcellular localization signal, tumor suppressor protein, growth factor, membrane protein, receptor, vasoactive protein or peptide, antiviral protein or ribozyme, or a derivative thereof, or a micro-RNA.

The purification methods provided herein can not only effectively remove process-related impurities (such as HCPs, HCDs), but also retain the activity of the viruses to the greatest extent. In addition, the methods provided herein are suitable for large-scale and cost-effective production of the viral vectors, such as lentiviral vectors. In certain embodiments, the preparation of the recombinant virus particles obtained using the purification methods provided herein contains less than 10 μg/ml, less than 5 μg/ml, less than 4 μg/ml, less than 3 μg/ml, less than 2 μg/ml, less than 1 μg/ml or less than 0.5 μg/ml proteins derived from the suspension cells (i.e., HCP) and/or less than 3 μg/ml, less than 2.5 μg/ml, less than 2 μg/ml, less than 1.5 μg/ml, less than 1 μg/ml, less than 0.8 μg/ml, or less than 0.4 μg/ml DNAs derived from the suspension cells (i.e., HCD). In certain embodiments, the preparation of the recombinant virus particles obtained using the purification methods provided herein is capable of infecting a population of host cells rendering more than 40%, more than 45%, more than 50%, more than 55%, more than 60%, more than 65%, more than 70%, more than 75%, more than 80% or more than 85% of the host cells expressing the therapeutic protein or fragment thereof at a multiplicity of infection (MOI) of no more than 5, no more than 4, no more than 3, no more than 2, or no more than 1.

As used herein, the term "multiplicity of infection" or "MOI" with respect to recombinant virus particles refers to the ratio of recombinant virus particles: host cells used during transfection of host cells. A MOI value with respect to the recombinant virus particles indicates how much recombinant virus particles is going to be used in a given infection. For example, if 1,000,000 recombinant virus particles are used to transfect 100,000 host cells, the multiplicity of infection (MOI) is 10. The MOI can be measured using conventional techniques known in the art, such as polymerase chain reaction (PCR), fluorescent antibody staining (FA), indirect fluorescent antibody staining (IFA), and enzyme linked immunosorbant assay (ELISA).

Importantly, the methods provided herein are more effective as compared to conventional purification methods. In particular, the methods provided herein take only about 6-8 hours to complete the purification process, which is much quicker than the conventional purification methods, which would generally take about 2 days).

The recombinant virus particles suitable for the method provided herein can be any virus or viral-like particles, such as retrovirus (e.g., lentivirus), adenovirus, adeno-associated virus (AAV), herpesvirus (e.g., herpes simplex virus), poxvirus, baculovirus, papillomavirus, papovavirus (e.g., SV40), HCV, HPV or inactivated virus vaccine (e.g., COVID 19 vaccines and Rabies vaccines). The retrovirus can be selected from the group consisting of alpha retroviruses, delta retroviruses, beta retroviruses, gamma retroviruses, the different types of simian immunodeficiency viruses, epsilon retroviruses, spumavirus, primate lentiviruses such as the different types of human immunodeficiency viruses (HIV for human immunodeficiency virus), non-primate mammal lentiviruses such as the equine infectious anemia virus, the caprine arthritis-encephalitis virus, the feline immunodeficiency virus, and the ovine visnamaedi virus.

It's noteworthy that the methods provided herein are suitable for low-quality samples, for example, those with complex virus supernatant having high level of impurities and low virus titer, which is often the case for lentivirus samples. It would be appreciated that the methods provided herein can also be used for purifying good-quality samples with less fragile viruses, such as AAV. It would also be appreciated that methods suitable for purifying less fragile viruses (such as AAV) known in the art would not be necessarily suitable for purifying low-quality samples with fragile viruses, such as lentiviruses.

The methods provided herein are described in detail below:

1. Sample

The method provided herein comprises obtaining a sample comprising the recombinant virus particles. In some embodiments where the recombinant viruses are lentiviruses, the sample is obtained from a supernatant of cell culture, as lentiviruses are packaged in packaging cells and then secreted from the packaging cells into a suspension. The recombinant virus particles can be harvested from the supernatant of the culture according to methods well known in the field. In certain embodiments, the sample comprises clarified supernatant. In some embodiments where the recombinant viruses are other viruses, such as adenoviruses or AAV, the packaging cells comprising the recombinant virus particles may need to be lysed and the sample shall be obtained from the cell lysate. The recombinant virus particles can be harvested from the cell lysate according to methods well known in the field.

The packaging cells can be cultured in a cell culture medium suitable for cultivation of mammalian cell and for producing the recombinant virus particles. The packaging cells used for packaging the recombinant virus particles can be cultured either in an adherent manner or in a non-adherent manner (i.e., in suspension). In certain embodiments, the sample is prepared from a culture of suspension cells. Culture of suspension cells may be conducted for instance in dishes, flask (e.g., shake flask), roller bottle or in bioreactors (e.g., WAVE bioreactor, stirred bioreactor), using, for example, batch, fed-batch, continuous systems, hollow fiber, and the like. Suspension cells for packaging the recombinant virus particles were preferably used to achieve large scale production of the recombinant virus particles through cell culture, which are preferably cultured in the absence of animal- or human-derived serum or components thereof. Suitable conditions for culturing cells are well known in the art, see, for example, *Tissue Culture, Academic Press, Kruse and Paterson, editors* (1973), and *R. I. Freshney, Culture of animal cells: A manual of basic technique, fourth edition* (Wiley-Liss Inc., 2000, ISBN 0-471-34889-9).

In certain embodiments, the sample is prepared from a culture of adherent cells.

In certain embodiments, the sample comprises at least $1\times10^6$ transducing units/mL (TU/mL), at least $2\times10^6$ TU/mL, at least $4\times10^6$ TU/mL, at least $6\times10^6$ TU/mL, at least $8\times10^6$ TU/mL, at least $1\times10^7$ TU/mL, at least $5\times10^7$ TU/mL, at least $1\times10^8$ TU/mL, at least $5\times10^8$ TU/mL, at least $1\times10^9$ TU/mL, at least $5\times10^9$ TU/mL, or at least $1\times10^{10}$ TU/mL recombinant virus particles. The titer of the recombinant virus particles can be measured by any conventional methods known in the art, for example, FACS or qPCR.

2. Two-Step Chromatography

The method provided herein comprises a two-step chromatography, comprising the combination of an SEC purification step (i.e., the SEC step) and an SXC purification step (i.e., the SXC step). In certain embodiments, the SEC step is performed prior to the SXC step. In other embodiments, the SEC step is performed after the SXC step. The order of the SEC step and SXC step can be determined by the recovery rate of the recombinant virus particles after purification. For example, if the recovery rate of the recombinant virus particles is less than 50% when SXC step is performed prior to the SEC step, then the skilled person would perform the SEC step prior to the SXC step, and vice versa.

In certain embodiments, the SEC column used in the method provided herein comprises an SEC medium. As used herein, the term "size exclusion chromatography" or "SEC" refers to a method for separating materials according to molecular size using uniformly sized, porous, nonionic or ionic gels as a stationary phase. In general, materials that are smaller than the pore size enter the porous stationary phase and have a longer transit time, whereas materials that are larger than the pore size cannot enter the porous stationary phase and thus move fast together with the mobile phase. Accordingly, the impurities (e.g., HCP, HCD) in the suspension or lysate comprising the recombinant virus particles can be separated from the recombinant virus particles depending on the different sizes, where the impurities generally have a longer transit time than the recombinant virus particles as they are generally smaller than the recombinant virus particles and in some cases further because the impurities bind to the positively charged inner side of the pores of the porous stationary phase. Any commercially available SEC medium may be used to obtain a flow-through containing the recombinant virus particles.

In certain embodiments, the SEC medium is a multimodal chromatographic medium, such as Capto Core700, Lyer700, Capto Core400, Mix Q-90, Seplife Suncore 700, Monomix 500, or Monomix 1000. In certain embodiments, the SEC medium is Capto Core700, Lyer700, or Mix Q-90. In certain embodiments, the SEC medium is Lyer700.

As used herein, the term "steric exclusion chromatography" or "SXC" refers to a method for separating materials by constrained co-hydration chromatography. The principle of the SXC provided herein is similar to that described in Gagnon P. et al., *Principles and applications of steric exclusion chromatography, Journal of Chromatography A* 2014, 1324, 171-180, incorporated herein by reference, which relates to a high productivity purification of immunoglobulin G monoclonal antibodies on starch coated magnetic nanoparticles by steric exclusion with polyethylene glycol (PEG) as an alternative for packed chromatography columns. Briefly, the SXC separates impurities (e.g., HCPs, HCDs) from a sample (which is hydrated, for example, a solution comprising recombinant virus particles) by contacting the sample with an SXC medium having a hydrated surface and contacting the sample with a nonionic organic polymer (serving as a constraining agent) in an amount sufficient to cause at least a fraction (e.g., more than 50% to substantially all) of the target species (e.g., recombinant virus particles) to be retained at the hydrated surface of the SXC medium in a substantial absence of a direct chemical interaction between the target species and the hydrated surface of the SXC medium. As used herein, the term "hydrated surface" refers to a surface that interacts strongly with water, via, for example, hydrogen bonding, electrostriction, or combination thereof. Such interactions may be mediated by chemical groups such as hydroxyls, negative charges, positive charges, or uncharged polar groups.

The form of association described above is referred to as "constrained co-hydration". The conditions that provide the constrained co-hydration comprise pH, conductivity and salt concentration of buffers delivered to the SXC column that discourage direct interaction between the hydrated target species and the SXC medium. Details can be found in, for example, Gagnon P. et al., *Principles and applications of steric exclusion chromatography, Journal of Chromatography A* 2014, 1324, 171-180, which is incorporated herein by reference.

As used herein, the term "nonionic organic polymer" refers to a naturally occurring or synthetic hydrocarbon comprising linked repeating organic subunits that lack charged groups. The nonionic organic polymer can be a non-ionic surfactant or non-ionic organic polymer having a hydrophobic part and a hydrophilic part. Exemplary nonionic organic polymer includes, but not limited to, an aliphatic polyether, such as polyalkylene glycol (PAG), in particular a PEG, or a polypropylene glycol, or a poloxamer. In certain embodiments, the nonionic organic polymer is PEG. The PEG can be a PEG having an average molecular weight between about 4,000 (PEG4000) grams per mole and about 15,000 (PEG15000), preferably between about 4,000 (PEG4000) grams per mole and about 8,000 (PEG8000). In certain embodiments, the PEG has an average molecular weight of about 6,000 (PEG6000) grams per mole. The concentration of the non-ionic organic compound, for example in the form of PAG (e.g., PEG and polypropylene glycol) in the sample contacted with the SXC medium varies based on the specific recombinant virus particles to be purified, for example, in a range of from 0.1-50% (w/v), 1-40% (w/v), 2-30% (w/v), 3-20% (w/v), or 10-15% (w/v). The size and amount of the nonionic organic polymer in form of the PAG, such as PEG or polypropylene glycol or mixtures thereof, depend on the size and the shape of the recombinant virus particles. For example, in cases of larger recombinant virus particles, smaller PAG (e.g., PEG) with lower average molecular masses will be used; in cases of smaller recombinant virus particles, PAG with higher average molecular masses will be used. For another example, in cases of larger recombinant virus particles, the concentration of the PAG (e.g., PEG, polypropylene glycol or mixtures thereof) is lower; in cases of smaller recombinant virus particles, the concentration of PAG is higher.

The presence of the nonionic organic polymer may be achieved via mixing the sample (e.g., a supernatant or lysate comprising the recombinant virus particles, or a flow-through liquid obtained from the SEC step of the two-step chromatography as described above) with the nonionic organic polymer as described above.

In certain embodiments, the SXC medium is a hydrophilic medium comprising one or more hydratable chemical groups. In certain embodiments, the SXC medium is selected from the group consisting of: 4FF, 6FF, and other commercially available medium. In certain embodiments, the SXC medium is Sepharose 4FF, Sepharose 6FF, Bestarose 4FF, Bestarose 6FF, NW Rose 4FF, NW Rose 6FF, NW Dex G-25, NW Super 75, NW Super 100, NW Super 150, NW Super 200, Seplife 6B, Seplife 4FF, Seplife 6FF, Seplife G25, Seplife G75, or Seplife G100. The SXC medium used in the present disclosure is much more cost-effective and/or more scalable than that used in Gagnon P. et al., *Principles and applications of steric exclusion chromatography, Journal of Chromatography A* 2014, 1324, 171-180. and Pavel Marichal-Gallardo et al., *Steric exclusion chromatography for purification of cell culturederived influenza A virus using regenerated cellulose membranes and polyethylene glycol, Journal of Chromatography A Volume* 1483, 3 Feb. 2017, Pages 110-119, all of which are incorporated herein by reference. For example, the cellulose membrane used in Pavel Marichal-Gallardo et al is difficult to be adapted for large-scale purification, and currently few commercially available SXC medium exists for large-scale purification of recombinant virus particles.

For the SXC used in the methods provided herein, the impurities including HCPs and HCDs are present in the effluent and the washing buffer while the recombinant virus particles remain in or on the SXC medium. The recombinant virus particles present in or on the SXC medium may be eluted with an elution buffer in absence of any nonionic organic polymer or comprising a reduced amount of the nonionic organic polymer compared to the sample or the washing buffer. The preparation of recombinant virus particles does not contain any nonionic organic polymers.

In certain embodiments, the elution buffer comprises a NaCl of 0.3-0.5 mol/l (e.g., 0.4 mol/l). In certain embodiments, the elution buffer does not comprise nonionic organic polymer (e.g., PEG). As can be seen, the salt concentration of the elution buffer used in the method provided herein is significantly lower than that used in ion exchange chromatography, which requires a NaCl salt concentration of, for example, 0.6-1 mol/L to elute the viral vectors (e.g., lentiviral vectors) bound to the chromatographic medium. The reduction in the salt concentration used in the elution buffer would significantly reduce the shear force experienced by the recombinant viruses, and thus reduce the loss of viral activity. In certain embodiments, the SXC medium is 4FF. In certain embodiments, the nonionic organic polymer is PEG6000.

Contrarily to SEC, the SXC used in the methods provided herein does not require column packing, such that a much higher productivity can be achieved due to the higher flow rates. Contrarily to affinity chromatography, either bead-based or membrane-based, the SXC used in the methods provided herein does not require a medium with affinity ligands, which can be expensive to manufacture or to couple to an existing membrane (one of the reasons for increasing production costs). In addition, in ion exchange chromatography, virus stability would be compromised by high concentration of salt, and the virus product can only be recovered in a particular buffer composition.

Accordingly, exploitation of the SXC step in the scalable method provided herein has the following advantages: first, it avoids dilution effect on the final recombinant viral preparation (which is a drawback of a size exclusion chromatography); second, it does not require high salt elution buffer to elute the bound recombinant viruses such that the damage to the recombinant viruses are significantly reduced; third, it greatly reduces the volume and time of liquid handling during the viral purification. Exploitation of the SXC step in the methods provided herein at least partially contributes to the high recoveries and low impurities. In addition, use of SXC in the methods provided herein reduced the purification time as compared to the time required merely using SEC or other column-based methods described in the art. Accordingly, the productivity can be significantly enhanced due to the easiness of the SXC.

In certain embodiments, the SEC column has a bed height of about 5-10 cm. In certain embodiments, the SXC column has a bed height of about 5-10 cm. Since viral vectors are fragile, prolonged contact of which with the purification medium, for example, via passing through a high column height (e.g., greater than 20 cm) may lead to shearing of the virus and cause virus losses. The bed height of the columns used in the two-step chromatography of the method provided herein is significantly lower than that used in the conventional methods. This would significantly reduce the time for the recombinant viruses to pass through the columns, i.e., reduce the friction time between the recombinant viruses and the medium, thereby reducing the damage to the recombinant viruses during the chromatographic purification step and maximize the viral activity retention.

In summary, the two-step chromatography used in the method provided herein can remove process-related impurities to the greatest extent, and in the meantime is relatively milder than that used in conventional purification methods thereby achieving high activity retention. In addition, the two-step chromatography is much more efficient than the chromatography used in conventional purification methods, which makes the method provided herein is attractive for industrial uses, such as large-scale purification of recombinant viruses for clinical uses. It's noteworthy that application of SXC in a scalable purification process for providing viruses for clinical uses has not been reported up to date. Hence, the present disclosure provides a novel and more efficient purification method, especially suitable for scalable purification of fragile viruses, such as lentiviruses.

3. Nuclease Digestion, Sterile Filtration, Ultrafiltration and Diafiltration

In certain embodiments, the method provided herein further comprises adding a nuclease (e.g., Benzonase (Merk) or BenzoNuclease (Novoprotein), or any other GMP endonucleases) to the cell culture before obtaining the supernatant or lysate. The nuclease can be added at a concentration of about 20-50 IU/mL. In other words, the recombinant virus particles packaged in suspension cells can be digested with nuclease in an online mode, i.e., adding nuclease to cell culture shake flask, WAVE bioreactor or stirred bioreactor before harvesting. The online nuclease digestion before virus harvest can reduce the purification time by about 1-2 hours.

In certain embodiments, the method provided herein further comprises subjecting the preparation of the recombinant virus particles to sterile filtration prior to ultrafiltration concentration and diafiltration, and after the two-step chromatography. The sterilization filtration step prior to ultrafiltration concentration and diafiltration can significantly improve the yield of the recombinant viruses. Without wishing to be bound by any theory, but it is believed that the concentrated viruses tend to be trapped on the filtration membrane due to its high concentration, thereby negatively affect the recovery rate of the recombinant viruses. However, sterile filtration conducted after the ultrafiltration concentration and diafiltration is also acceptable in some other embodiments. The sterile filtration can be performed by filtering the preparation of the recombinant virus particles through any suitable membrane known in the art, for example, a 0.22 um membrane.

In certain embodiments, the method provided herein further comprises ultrafiltration or diafiltration of the recombinant viruses after sterile filtration. The ultrafiltration can be performed using any methods known in the art. In certain embodiments, the ultrafiltration is performed using a tangential flow filtration, using, for example, a hollow fiber module (e.g., hollow fiber module having a pore size of 100-300 KD or 300-750 KD). Ultrafiltration or diafiltration can be performed using 300-750 KD hollow fibers in a closed-circuit mode to replace the solvent of the viral preparation with the virus freezing buffer and to concentrate it to a desired virus titer. Noteworthy, the ultrafiltration and diafiltration of the method provided herein are performed in a single combined step, which greatly reduces the time for the virus to be mechanically squeezed and sheared during the purification process, and thereby maximize the viral activity retention. The buffers used in the ultrafiltration step may be any buffers known in the art that are suitable for use in ultrafiltration, depending on the samples to be purified.

In another aspect, the present disclosure provides the use of the method provided herein for isolating recombinant virus particles, especially recombinant lentivirus particles, in a large-scale.

EXAMPLE 1

Purification of Lentivirus Vectors expressing CAR1

The lentivirus vectors expressing CAR1 were collected and purified according to the following steps:

1. Resuscitation of suspended 293T cells: inoculated 125 mL Shake flask with $0.5 \times 10^6$ cells/mL; the inoculation volume was 20~30 mL; the complete medium was Transpro CD01 (Shanghai Duoning)+4 mM GlutaMax (Thermo); and shake cultured at 37° C. for 3 days.

2. Cell expansion: inoculated with $0.2~0.5 \times 10^6$ cells/mL, cultured for 2~3 days for expansion culture, followed by inoculating 60 mL in 250 mL shake flask, inoculating 120 mL in 500 mL shake flask, inoculating 240 mL in 1000 mL shake flask, and inoculating 500~720 mL in 3000 mL shake flask, respectively.

3. WAVE 10 cell culture bag inoculation (Sartorius): inoculated with $0.2\times10^6$ cells/mL; the inoculation volume was 1.6 L; after culturing for 72 h, used complete medium to dilute the cell density to $1.8\times10^6$ cells/mL, and continued to culture for 24 h .

4. After culturing for 24 hours, set the final transfected cell density to $3\times10^6$ cells/mL, the final volume of virus packaging to 2 L, the plasmid dosage to be 1.5 μg/mL, and the plasmid ratio to CAR1 transfer plasmid: gag/pol plasmid: VSV-g plasmid: REV plasmid=2:1:1:1.

5. After transfection for 47 h, added 2 mM $MgCl_2$ to WAVE, then added nuclease BenzoNuclease (Novoprotein) to a final concentration of 50 IU/mL, then continued cell culture for 60 min, and completed nuclease digestion at the same time.

6. Harvest and Clarification: Cells were harvested at 48 h, centrifuged at 1500 g for 15 min, and then clarified using a Sartopure® PP3 (0.45 μm, 17.3 $cm^2$, Sartorius) clarification filter.

7. SXC chromatography:

(1) A 50 mm diameter SEC column was loaded with 8 cm of 4FF chromatography medium (Shanghai BestChrom), and equilibrated with Equilibration Buffer (10 mM PB+150 mM NaCl+4% sucrose+12% PEG6000, pH 7.0) with 5~10 Column Volumes (CV).

(2) Added PEG6000 to the clarified sample to a final concentration of 12%, and mixed thoroughly.

(3) Sample loading: The sample containing 12% PEG6000 was passed through the SEC column at a flow rate of 60 cm/h, using an AKTA Pure 150 chromatography system (Cytiva).

(4) After the sample was loaded, rinsed the sample with Equilibration Buffer to make the base line horizontal.

(5) Elution: used an elution buffer (10 mM PB+150 mM NaCl+4% sucrose+0.4 M NaCl, pH 7.0) for elution, and collected elution peaks.

8. SEC multimodal chromatography (Diamond Layer 700, BestChrom):

(1) Used buffer (10 mM PB+150 mM NaCl+4% sucrose, pH 7.2) to dilute the SXC-eluted sample obtained from step 7 above to 5 folds and mixed well.

(2) Loaded 10 cm of Diamond Layer 700 SEC multimodal chromatographic medium into a 35 mm column, and equilibrated it with buffer (10 mM PB+150 mM NaCl+4% sucrose, pH 7.2).

(3) Purification: Passed the 5-fold diluted sample through the Layer 700 chromatography medium at a flow rate of 200 cm/h and collected the flow-through peak. After the completion of the sample loading, continued to flush $A_{280}$ to baseline with a buffer (10 mM PB+150 mM NaCl+4% sucrose, pH 7.2).

9. Sterile filtration: Supor® EKV—Mini Kleenpak™ Capsules sterilization filtration membrane (375 cm2, Pall) was used to sterilize the samples obtained from the Layer 700 chromatography.

10. 500 KD UF/DF ultrafiltration concentration and diafiltration:

Used Minikros® 500 KD (790 $cm^2$, Repligen) to concentrate to 5~8 times, which was followed by using buffer (10 mM PB+150 mM NaCl+4% sucrose, pH 7.2) for diafiltration. Diafiltrated with 5~10 volumes, and then further concentrated to about 5 times. As such, the entire purification process was completed.

The purified lentivirus vectors were used to transfect a host cell. In particular, healthy human PBMC cells were resuscitated and activated using Dynabeads CD3/CD28 magnetic beads. Following this, the activated PBMC cells were transfected with the purified lentivirus at MOI=3, cultured to day7, and sampled to detect the positive rate of CAR1 expressing.

Figure 2A:
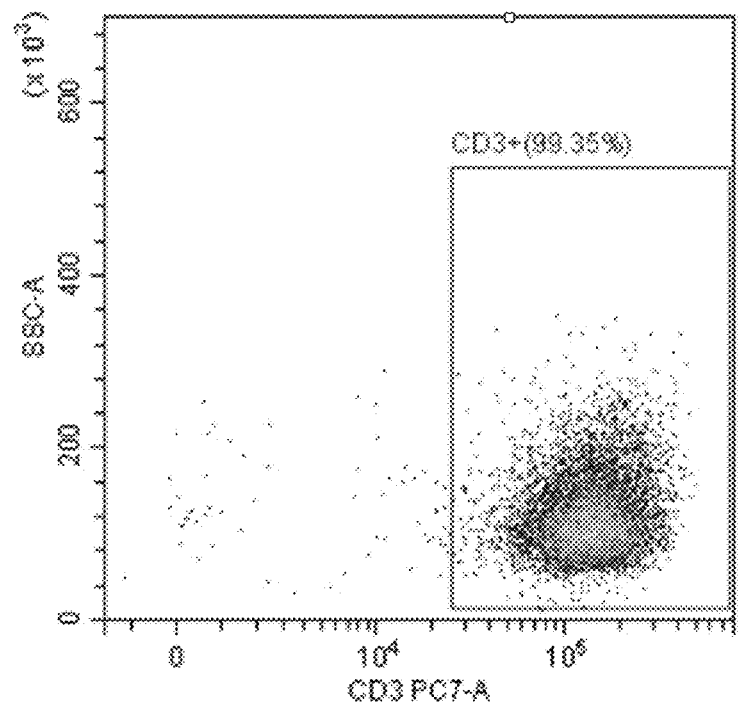
FIGS. 2A, 2B and 2C show the transfection efficiency of the lentivirus purified using the method of the present disclosure in one embodiment (Case 1).
Figure 2B:
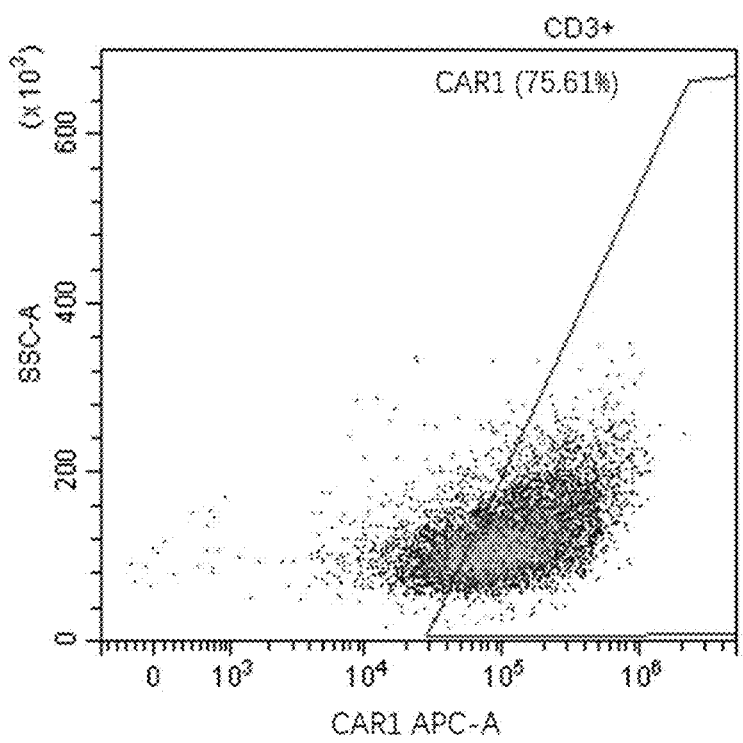
Figure 2C:
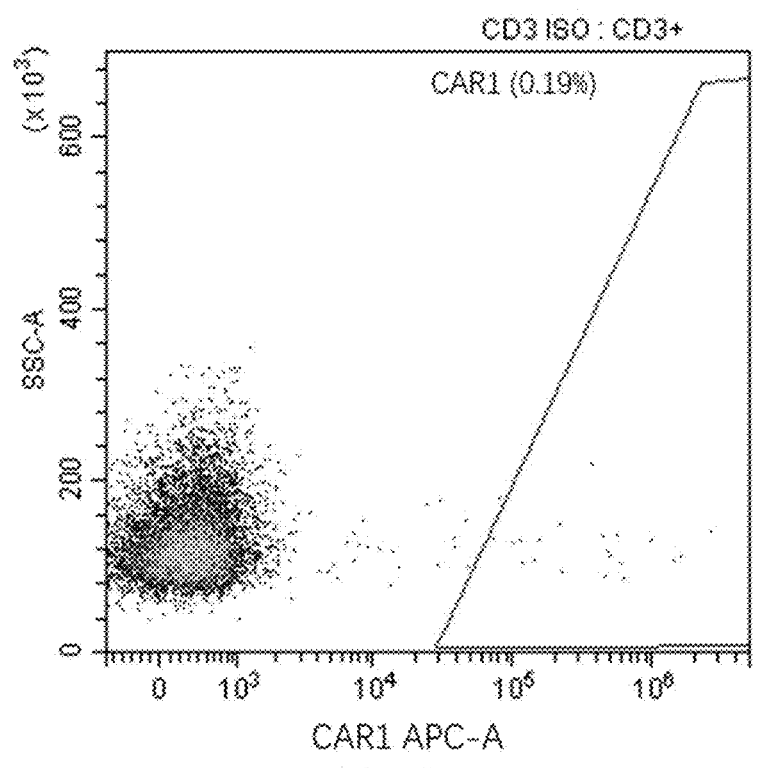

It was found that up to 75.61% of the host cells expressed CAR1 on surfaces thereof using the purified lentivirus vectors at an MOI of 3 (FIG. 2B). In contrast, for the lentivirus vectors purified using the conventional purification method (see, FIG. 1, left panel), an MOI of 8 of the recombinant lentivirus particles were required to transfect the host cells to have 70% of the host cell expressing CAR. FIG. 2C shows the ISO control for the CAR1 expression using non-specific isotype antibody detection. These data suggest that the lentivirus vectors purified using the method described herein retain higher activity compared to those purified using conventional purification method.

EXAMPLE 2

Purification of Lentivirus Vectors expressing CAR2

The lentivirus vectors expressing CAR2 were collected and purified according to the following steps:

1. Resuscitation of suspended 293T cells: inoculated 125 mL Shake flask with $0.5\times10^6$ cells/mL; the inoculation volume was 20~30 mL; the complete medium was Transpro CD01 (Shanghai Duoning)+4 mM GlutaMax (Thermo); and shake cultured at 37° C. for 3 days.

2. Cell expansion: inoculated with $0.2$~$0.5\times10^6$ cells/mL, cultured for 2~3 days for expansion culture, followed by inoculating 60 mL in 250 mL shake flask, inoculating 120 mL in 500 mL shake flask, inoculating 240 mL in 1000 mL shake flask, and inoculating 500~720 mL in 3000 mL shake flask, respectively.

3. WAVE 10 cell culture bag inoculation (Sartorius): inoculated with $0.2\times10^6$ cells/mL; the inoculation volume was 1.6 L; after culturing for 72 h, used complete medium to dilute the cell density to $1.8\times10^6$ cells/mL, and continued to culture for 24 h.

4. After culturing for 24 hours, set the final transfected cell density to $3\times10^6$ cells/mL, the final volume of virus packaging to 2 L, the plasmid dosage to be 1.0 μg/mL, and the plasmid ratio to CAR2 transfer plasmid: gag/pol plasmid: VSV-g plasmid: REV plasmid=3:1:11.

5. After transfection for 47 h, added 2 mM MgCl 2 to WAVE, then added nuclease BenzoNuclease (Novoprotein) to a final concentration of 50 IU/mL, then continued cell culture for 60 min, and completed nuclease digestion at the same time.

6. Harvest and Clarification: Cells were harvested at 48 h, centrifuged at 1500 g for 15 min, and then clarified using a Sartopure® PP3 (0.45 μm 17.3 $cm^2$, Sartorius) clarification filter.

7. SXC chromatography:

(1) A 50 mm diameter SEC column was loaded with 8 cm of 4FF chromatography medium (Shanghai BestChrom), and equilibrated with Equilibration Buffer (10 mM PB+150 mM NaCl+12% PEG6000, pH 7.0) with 5~10 Column Volumes (CV).

(2) Added PEG6000 to the clarified sample to a final concentration of 12%, and mixed thoroughly.

(3) Sample loading: The sample containing 12% PEG6000 was passed through the SEC column at a flow rate of 60 cm/h, using an AKTA Pure 150 chromatography system (Cytiva).

(4) After the sample was loaded, rinsed the sample with Equilibration Buffer to make the base line horizontal.

(5) Elution: used an elution buffer (10 mM PB+150 mM NaCl+0.4 M NaCl, pH 7.0) for elution, and collected elution peaks.

8. SEC multimodal chromatography (Diamond Layer 700, BestChrom):

(1) Used buffer (10 mM PB+150 mM NaCl, pH 7.2) to dilute the SXC-eluted sample obtained from step 7 above to 5 folds and mixed well.

(2) Loaded 10 cm of Diamond Layer 700 SEC multimodal chromatographic medium into a 35 mm column, and equilibrated it with buffer (10 mM PB+150 mM NaCl, pH 7.2).

(3) Purification: Passed the 5-fold diluted sample through the Layer 700 chromatography medium at a flow rate of 200 cm/h and collected the flow-through peak. After the completion of the sample loading, continued to flush A280 to baseline with a buffer (10 mM PB+150 mM NaCl, pH 7.2).

9. Sterile filtration: Supor® EKV—Mini Kleenpak™ Capsules sterilization filtration membrane (375 cm2, Pall) was used to sterilize the samples obtained from the Layer 700 chromatography.

10. 500 KD UF/DF ultrafiltration concentration and diafiltration:

Used Minikros® 500 KD (790 cm$^2$, Repligen) to concentrate to 5~8 times, which was followed by using buffer (10 mM PB+150 mM NaCl+4% sucrose, pH 7.2) for diafiltration. Diafiltrated with 5~10 volumes, and then further concentrated to about 5 times. Human albumin was supplemented to a final concentration of 0.5% to provide the final virus product.

The purified lentivirus vectors were used to transfect a host cell. In particular, healthy human PBMC cells were resuscitated and activated using Dynabeads CD3/CD28 magnetic beads. Following this, the activated PBMC cells were transfected with the purified lentivirus at MOI=3, cultured to day7, and sampled to detect the positive rate of CAR2 expressing.

Figure 3A:
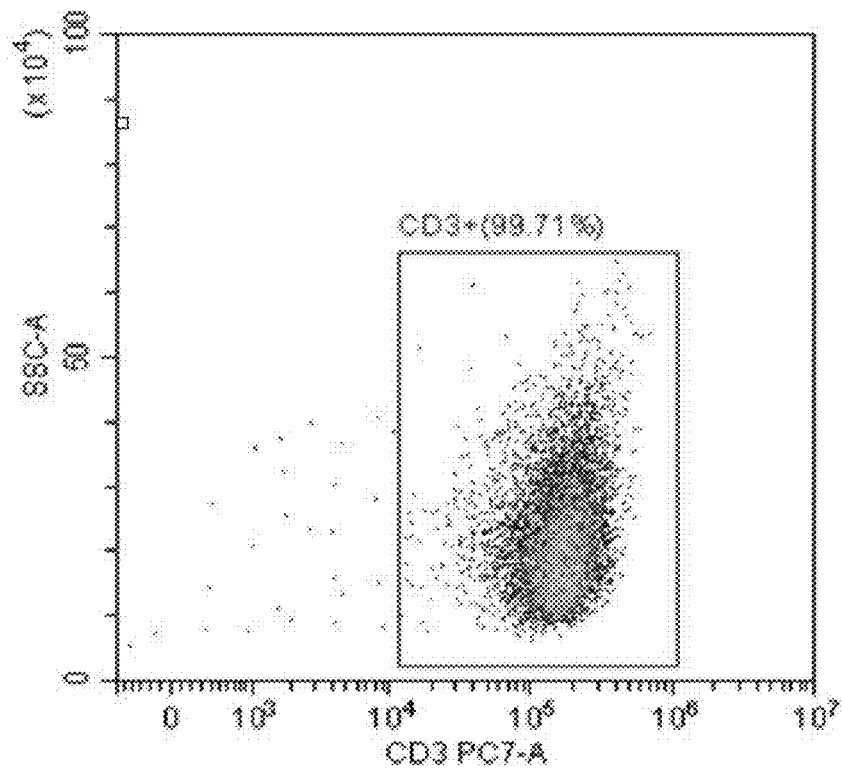
FIGS. 3A, 3B and 3C show the transfection efficiency of the lentivirus purified using the method of the present disclosure in another embodiment (Case 2).
Figure 3B:
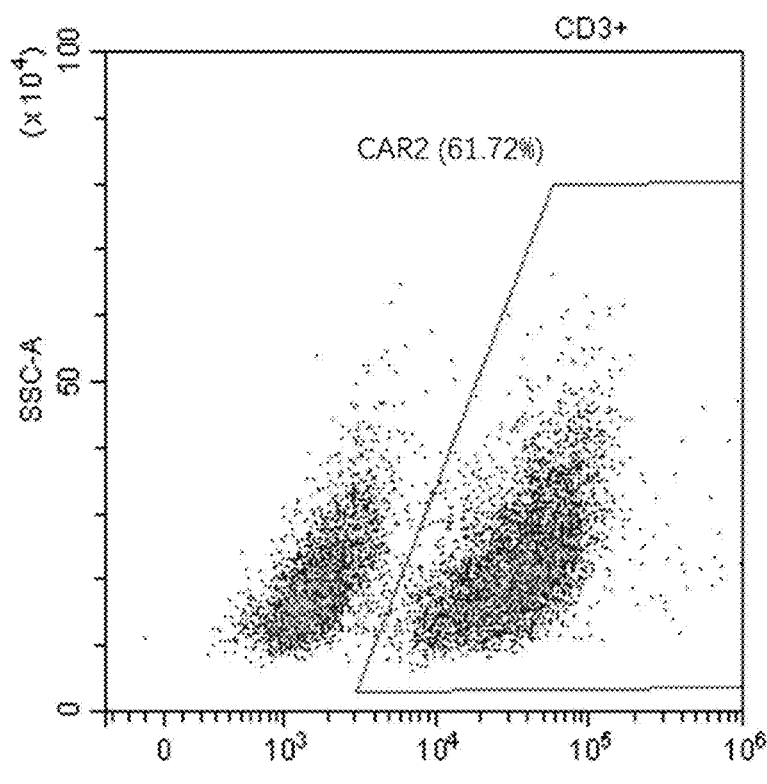
Figure 3C:
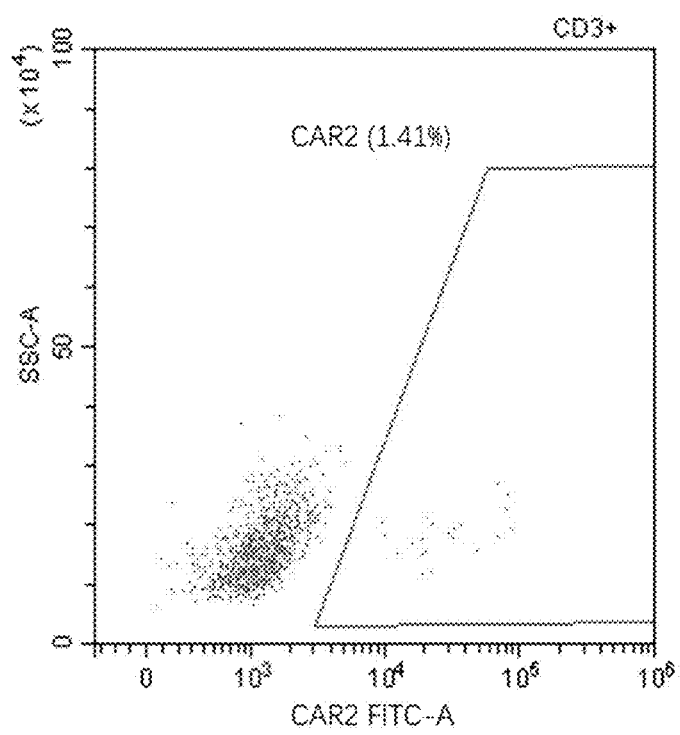

It was found that up to 61.72% of the host cells expressed CAR2 using the purified lentivirus vectors at an MOI of 3 (FIG. 3B). In contrast, for the lentivirus vectors purified using the conventional purification method (see, FIG. 1, left panel), the percentage of CAR-expressing host cells transfected with such purified lentivirus vectors at an MOI of 3 reduced to less than 50%. FIG. 3C shows the ISO control for the CAR2 expression using non-specific isotype antibody detection. These data suggest that the lentivirus vectors purified using the method described herein retain higher activity compared to those purified using conventional purification method.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A method of purifying a population of recombinant lentivirus particles, said method comprising:
obtaining a sample comprising the recombinant lentivirus particles and a contaminant;
subjecting the sample to a steric exclusion chromatography (SXC) column comprising a hydrophilic medium in the presence of polyethylene glycol (PEG) rendering the recombinant lentivirus particles bound to the hydrophilic medium;
eluting the SXC column with an elution buffer to obtain a preparation of the recombinant lentivirus particles; and
subjecting the preparation of the recombinant lentivirus particles to a multimodal chromatography column comprising a multimodal chromatographic medium which retains the contaminant;
collecting a flow-through liquid from the multimodal chromatography column, wherein the flow-through liquid comprises the recombinant lentivirus particles,
wherein the method does not comprise a step which retains the recombinant lentivirus particles to an ion exchange chromatography column.

2. The method of claim 1, wherein the multimodal chromatographic medium is selected from the group consisting of: Capto Core700, Capto Core400, Mix Q-90, Seplife Suncore 700, Monomix 500 and Monomix 1000.

3. The method of claim 1, wherein the multimodal chromatography column has a bed height of about 5-10 cm.

4. The method of claim 1, wherein the hydrophilic medium is selected from the group consisting of: 4FF, 6FF, NW Dex G-25, NW Super 75, NW Super 100, NW Super 150, NW Super 200, Seplife 6B, Seplife G25, Seplife G75 and Seplife G100.

5. The method of claim 1, wherein the SXC column has a bed height of about 5-10 cm.

6. The method of claim 1, wherein the elution buffer comprises a NaCl of 0.3-0.5 mol/l.

7. The method of claim 1, wherein the PEG has an average molecular weight between about 4,000 grams per mole and about 15,000 grams per mole.

8. The method of claim 7, wherein the PEG has an average molecular weight of about 6,000 grams per mole.

9. The method of claim 8, wherein the PEG has a concentration of about 10-15% (w/v).

10. The method of claim 1, wherein the recombinant lentivirus comprises a transgene encoding a therapeutic protein or fragment thereof.

11. The method of claim 10, wherein the therapeutic protein is selected from the group consisting of: chimeric antigen receptor (CAR), an enzyme, cytokine, chemokine, hormone, antibody, anti-oxidant molecule, engineered immunoglobulin-like molecule, single chain antibody, fusion protein, immune co-stimulatory molecule, immunomodulatory molecule, a transdomain negative mutant of a target protein, toxin, conditional toxin, antigen, transcription factor, structural protein, reporter protein, subcellular localization signal, tumor suppressor protein, growth factor, membrane protein, receptor, vasoactive protein or peptide, anti-viral protein or ribozyme, or a derivative thereof, or a micro-RNA.

12. The method of claim 1, wherein the sample comprises at least 1×10$^6$ TU/ml recombinant lentivirus particles.

13. The method of claim 1, wherein the sample is prepared from a culture of a suspension cells.

14. The method of claim 13, wherein the suspension cells are selected from the group consisting of HEK293 T cells, HEK293 cells and 293 EBNA-1 cells.

15. The method of claim 13, further comprising adding a nuclease to the culture before preparing the sample.

16. The method of claim 13, wherein the contamiant is proteins or DNAs derived from the suspension cells, wherein the population of recombinant lentivirus particles after purification contains less than 1 ug/ml proteins derived from the suspension cells and/or less than 0.8 ug/ml DNAs derived from the suspension cells.

17. The method of claim 10, wherein the population of recombinant lentivirus particles after purification are capable of infecting a population of host cells rendering more than 70% of the host cells expressing the therapeutic protein or fragment thereof at a multiplicity of infection (MOI) of no more than 3.

18. The method of claim 1, further comprising subjecting the flow-through liquid comprising the recombinant lentivirus particles to sterile filtration, ultrafiltration or diafiltration.

19. The method of claim 18, wherein the ultrafiltration is a tangential flow filtration.

20. The method of claim 19, wherein the tangential flow filtration is carried out by a hollow fiber module.

21. A method of purifying a population of recombinant lentivirus particles, said method comprising:
   obtaining a sample comprising the recombinant lentivirus particles and a contaminant;
   subjecting the sample to a multimodal chromatography column comprising a multimodal chromatographic medium which retains the contamiant;
   collecting a flow-through liquid from the multimodal chromatography column, wherein the flow-through liquid comprises the recombinant lentivirus particles;
   subjecting the flow-through liquid to a SXC column comprising a hydrophilic medium in the presence of a PEG rendering the recombinant lentivirus particles bound to the hydrophilic medium; and
   eluting the SXC column with an elution buffer to obtain a preparation of the recombinant lentivirus particles,
   wherein the method does not comprise a step which retains the recombinant lentivirus particles to an ion exchange chromatography column.

22. The method of claim 4, wherein the 4FF is selected from the group consisting of Sepharose 4FF, Bestarose 4FF, NW Rose 4FF, Seplife 4FF, and wherein the 6FF is selected from the group consisting of Sepharose 6FF, Bestarose 6FF, NW Rose 6FF, Seplife 6FF.

23. The method of claim 7, wherein the PEG is between about 4,000 grams per mole and about 8,000 grams per mole.

24. The method of claim 13, wherein the sample comprises clarified supernatant.

25. The method of claim 20, wherein the hollow fiber module has a pore size of 300-750 KD.

* * * * *